(12) United States Patent
Castro (10) Patent No.: US 11,432,829 B2
(45) Date of Patent: Sep. 6, 2022

(54) IMPLANT FOR BONE (71) Applicant: Blue Sky Technologies, LLC, Louisville, KY (US)

(72) Inventor: Frank Castro, Louisville, KY (US)

(73) Assignee: BLUE SKY TECHNOLOGIES, LLC, Louisville, KY (US)

( * ) Notice: Subject to any disclaimer, the term of this patent is extended or adjusted under 35 U.S.C. 154(b) by 0 days.

(21) Appl. No.: 16/901,459

(22) Filed: Jun. 15, 2020

(65) Prior Publication Data
US 2020/0305896 A1 Oct. 1, 2020

Related U.S. Application Data (63) Continuation-in-part of application No. 16/648,518, filed as application No. PCT/US2019/054383 on Oct. 3, 2019.

(60) Provisional application No. 62/809,670, filed on Feb. 24, 2019.

(51) Int. Cl.
*A61B 17/70* (2006.01)
*A61B 17/16* (2006.01)

(52) U.S. Cl.
CPC .......... *A61B 17/1671* (2013.01); *A61B 17/70* (2013.01)

(58) Field of Classification Search
CPC ................ A61B 17/70; A61B 17/1671; A61B 17/7032–17/7037; A61B 17/8625
See application file for complete search history.

(56) References Cited

U.S. PATENT DOCUMENTS

| | | |
|---|---|---|
| 3,887,186 A | 2/1975 | Matlock, Jr. |
| 4,244,689 A | 1/1981 | Ashman |
| 6,159,211 A | 12/2000 | Boriani et al. |
| 6,447,525 B2 | 9/2002 | Follmer et al. |
| 6,743,255 B2 | 5/2004 | Ferree |
| 6,746,484 B1 | 6/2004 | Liu et al. |
| 8,100,972 B1 | 1/2012 | Bruffey et al. |
| 9,636,232 B2 | 5/2017 | Neubardt |
| 9,707,100 B2 | 7/2017 | Afferzon et al. |
| 9,814,483 B2 | 11/2017 | Vardi |
| 9,867,733 B2 | 1/2018 | Mohan et al. |
| 10,166,033 B2 * | 1/2019 | Reiley ................. A61B 17/1757 |
| 2002/0055738 A1 * | 5/2002 | Lieberman ............. A61B 17/70 623/17.11 |
| 2004/0078079 A1 | 4/2004 | Foley |
| 2004/0133279 A1 | 7/2004 | Krueger et al. |
| 2005/0119753 A1 | 6/2005 | McGahan et al. |
| 2009/0254125 A1 | 10/2009 | Predick |
| 2009/0265006 A1 * | 10/2009 | Seifert ................. A61B 17/025 623/17.16 |
| 2011/0098747 A1 * | 4/2011 | Donner ................. A61F 2/4611 606/264 |
| 2011/0264229 A1 | 10/2011 | Donner |
| 2012/0010659 A1 | 1/2012 | Angert et al. |
| 2012/0232599 A1 | 9/2012 | Schoenly et al. |
| 2013/0150906 A1 | 6/2013 | Kerboul et al. |

(Continued)

FOREIGN PATENT DOCUMENTS

WO   WO2001085059   11/2001

*Primary Examiner* — Ellen C Hammond
(74) *Attorney, Agent, or Firm* — Business Patent Law, PLLC (57) ABSTRACT

The present invention is an implant for bone. The current implant is particularly useful in spinal surgical procedures.

12 Claims, 9 Drawing Sheets

(56) References Cited

U.S. PATENT DOCUMENTS

| | | | |
|---|---|---|---|
| 2014/0276835 A1* | 9/2014 | Tally | A61B 17/1604 |
| | | | 606/79 |
| 2016/0184099 A1 | 6/2016 | Gotfried | |
| 2016/0310294 A1 | 10/2016 | McConnell et al. | |
| 2017/0135733 A1* | 5/2017 | Donner | A61B 17/7058 |
| 2020/0405362 A1* | 12/2020 | Faulhaber | A61B 17/846 |
| 2021/0244455 A1* | 8/2021 | Castro | A61B 17/8605 |

\* cited by examiner

IMPLANT FOR BONE

PRIORITY

Applicant claims priority to U.S. application Ser. No. 16/648,518—Implant for Bone—filed Mar. 18, 2020, that claims priority to PCT/US2019/054383—Implant for Bone—, filed Oct. 3, 2019 that claims the benefit of U.S. Provisional Application No. 62/809,670—Implant for Bone—filed on Feb. 24, 2019.

BACKGROUND OF THE INVENTION

A. Field of the Invention

Among other things, the present invention is an implant for bone. The current implant is particularly suited for implantation into mammalian spinal tissues. The present implant is provided with a cutting blade. Select embodiments of the current invention include surface treatments in anticipation of improving attachment of bone to the implant.

B. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references.

References that may indicate a state-of-the-art for the current invention include: 1) U.S. Pat. No. 9,814,483-Vardi discloses a method and catheter for creating an interatrial aperture; 2) U.S. Pat. No. 3,887,186-Matlock, Jr. disclose a broadhead; 3) U.S. Pat. No. 8,199,972-Bruffey, et al. discloses a spinal cage having deployable member; 4) U.S. Pat. No. 4,244,689-Ashman discloses an endosseous plastic implant; 5) US Published Patent Application 20120232599-Schoenly, et al. discloses awl screw fixation members and related systems; 6) U.S. Pat. No. 9,636,232-Neubart discloses harvesting bone graft material for use in spinal and other bone fusion surgeries; 7) US Published Patent Application 20120010659-Angert, et al. discloses a facet fusion implant; 8) U.S. Pat. No. 6,447,525-Follmer, et al. discloses an apparatus and methods for removing material from a body lumen; 9) U.S. Pat. No. 8,070,819-Aferzon, et al. discloses an apparatus and method for anterior intervertebral spinal fixation and fusion; 10) U.S. Pat. No. 9,707,100-Duffield, et al. disclose an interbody fusion device and system for implantation; 11) U.S. Pat. No. 9,867,733-Mohan, et al. discloses a tissue adjustment implant; 12) US Published Patent Application 20040078079-Foley discloses systems and techniques for restoring and maintaining intervertebral anatomy; 13) US Published Patent Application 20090265006-Seifert, et al. discloses a lateral spinous process spacer; 14) US Published Patent Application 20160184099-Gotfried; 15) US Published Patent Application 20110264229-Donner discloses a sacroiliac joint fixation system; 16) US Published Patent Application 20130150906-Kerboul, et al. discloses a system and method for a lockable polyaxial driver tool; 17) US Published Patent Application 20090254125-Predick discloses a top loading polyaxial spine screw assembly with one step lockup; 18) WO2001085069-Lemaire, et al. discloses an anterior lumbar interbody implant; 19) U.S. Pat. No. 6,159,211-Boriani et al. discloses a stackable cage system for corpoectomy/vertebrectomy; 20) U.S. Pat. No. 6,743,255-Ferree discloses a spinal fusion cage with lordosis correction; 21) U.S. Pat. No. 6,746,484-Liu, et discloses a spinal implant; 22) US Published Patent Application 20040133279-Kruger, et al. discloses surgical implants for use as spinal spacers; 23) US Published Patent Application 2005/0119753-McGahan, et al. discloses an anterior impacted bone graft and driver instruments; and 24) 20160310294-McConnell et al. discloses a spinal fusion implant for oblique insertion.

SUMMARY OF THE INVENTION

The present invention provides a biocompatible implant for bone that can be interlocked with a device distinct from the implant. The current implant is also provided with a blade for cutting tissue. Preferred embodiments of the current fastener can also be utilized for transporting biocompatible devices/substances, such as adhesives, cameras, cannulas, fiber optics, implants, pharmaceuticals, etc. Preferred embodiments of the implant's blade are provided with an aperture. The aperture can assist tissue growth, such as bone, into and through the implant as well onto the inward surfaces of the implant. Select embodiments of the implant are provided with surface treatments in anticipation of improving attachment of bone to the implant.

With regard to spinal surgical procedures, prior art traditional fixation screws fixation stability is dependent on the healthy composition of the cancellous bone. Those skilled in the art recognize the healthy cortical bone is from about 20 to about 100 times stronger than healthy cancelleous bone. Those skilled in the art also know that increasing the screw length for osteoporotic bone rarely provides satisfactory resistance against the fixation screw from pulling-out or backing-out of bone. The blade of the current implant is shorter and wider than traditional fixation screws. Because of its novel structure and surgical insertion technique, the present implant has greater resistance against pulling-out or backing-out of osteoporotic bone. Further still, the blade's shorter length reduces the possibility of injury to nearby structures such as arteries, veins and nervous tissues. It is believed that the current invention's resistance to pull-out or back-out improves implant-construct stability, higher bone fusion rates and better postoperative clinical outcomes than prior art fixation screws.

For surgical procedures involving bone, the current implant can be inserted through a small linear aperture into the bone tissue. In one of the preferred uses of the current implant, subsequent to blade's surgical insertion into bone, the blade can be rotated up to 90 degrees relative to the plane of the surgical incision. Among other things, rotation of the blade increases resistance against pull-out or back-out of the blade from bone when compared to prior art fixation screws. It is also believed that the width of the implant's blade can contact a greater surface area of healthier cortical bone distinct from the surgically created cavity, thereby improving the possibility of successful postoperative bone fusion relative to prior art fixation screws.

Within the scope of the current invention, blades can be of symmetrical or asymmetrical configuration.

Symmetrical blades are typically preferred when the inner cortex is straight—a straight inner cortex as viewed from a lateral X-ray perspective looking at the spine. Asymmetrical blades are generally preferred when the inner cortex is sloped as seen on a lateral X-ray or sagittal CT scan). Regardless of whether symmetrical or asymmetrical, implants within the scope of the current invention require insertion and subsequent rotation of the blade of up to 90 degrees relative to the plane of the surgical incision.

In use, any surgical connecting rods will generally be parallel to the blades. In a first example for a laminectomy and fusion procedure, connecting rods and the present implant's blades will be generally vertical. In a second example for a laminoplasty procedure, the connecting rods and current implant's blades will be horizontal extending from the right side of the spinal elements to the left side spinal elements. The surgical incision will be up to 90 degrees offset from the final orientation of the implant's blade.

Various asymmetrical blade configurations are typically preferred when the surgical insertion corridor is not cylindrical. By way of illustration, when the current device is implanted into the posterior cervical facets, the blade is initially inserted through the posterior cortex perpendicular to the axis of the spinal cord. After insertion, the blade is rotated up to 90 degrees to be parallel to the axis of the spinal cord. It is believed that the asymmetrical blade allows for a greater surface area contact of the posterior cortex.

An aspect of the present invention is to provide an implant with a cutting blade.

Still another aspect of the present invention is to provide an implant with a blade that can be rotated up to 90 degrees relative to the surgical incision.

It is still another aspect of the present invention to provide an implant that improves resistance to pull-out or back-out and improves implant-construct stability, higher bone fusion rates and better postoperative clinical outcomes than prior art fixation screws.

Yet still another aspect of the present invention is to provide an implant with greater resistance against pulling-out or backing-out of osteoporotic bone that current fixation screws.

Still another aspect of the present invention is to provide an implant adapted for connection with a device distinct from the implant.

Yet another aspect of the present invention is to provide an implant with a conduit for transporting biocompatible devices/substances or chemotherapeutic agents.

It is still another aspect of the present invention to provide an implant with a blade having an aperture therein.

Yet still another aspect of the present invention is to provide an implant adaptable for use in the cervical region of the spine.

Still another aspect of the present invention is to provide an implant with a cutting wedge.

It is still another aspect of the present invention is to provide a shaft that is detachable from the cutting wedge.

Yet still another aspect of the present invention is to provide an implant with the cutting wedge that includes a graduated wedge-like cutting edge.

A preferred embodiment of the current invention can be described as an implant for bone adapted for interconnection with a device distinct from the implant; the implant comprising: a) a shaft comprising a first end and a second end opposite the first end; and b) a surgical cutting wedge connected to the first end of the shaft; the surgical cutting wedge comprising: i) a first planar surface and a second planar surface; ii) a first side connected with and perpendicular to the shaft, wherein the first side comprises a first end of greater height than an opposed second end of the first side; iii) a second side parallel to the first side, wherein a first end is of greater height than an opposed second end of the second side; iv) a third side extending between the first and second planar surfaces and first and second sides, wherein connection angles of first and second sides with opposed ends of the third side are identical; and v) a cutting edge opposed from and parallel to the third side; the cutting edge connected to the first planar surface, the second planar surface and the second ends of the first and second sides.

Another preferred embodiment of the current invention can be described as an implant for bone adapted for interconnection with a device distinct from the implant; the implant comprising: a) a surgical cutting wedge comprising: i) a first planar surface and a second planar surface; ii) an interconnected combination of a first side, a second side and a third side; the interconnected combination of the first, second and third sides extending between and connected to the first and second planar surfaces, wherein: the first side comprises a first end of greater height than an opposed second end of the first side; and the second side comprises a first end of greater height than an opposed second end of the second side; and iii) a cutting edge connected to the first and second planar surfaces and the second ends of the first and second sides such that the cutting edge is adapted to cut in perpendicular, clockwise and counterclockwise directions relative to a shaft; and b) a first end of the shaft connected to the first side of the surgical cutting wedge.

Still another preferred embodiment of the current invention can be described as an implant for bone adapted for interconnection with a device distinct from the implant; the implant comprising: a) a surgical cutting wedge comprising: i) a first planar surface and a second planar surface; ii) an interconnected combination of a first side, a second side and a third side; the interconnected combination of the first, second and third sides extending between and connected to the first and second planar surfaces; iii) a cutting edge connected to the first and second planar surfaces and the second ends of the first and second sides such that the cutting edge is adapted to cut in perpendicular, clockwise and counterclockwise directions relative to a shaft; iv) a catch, extending inward from first side toward the second side; the catch adapted to receive a detachable shaft; and v) opposed orifices extending from the catch through the first and second planar surfaces; b) the detachable shaft comprising; i) a first end releasably connected to catch of the surgical cutting wedge; and ii) an opening extending through the detachable shaft; and c) a pin extending through the opposed orifices and opening, thereby securing the detachable shaft.

It is the novel and unique interaction of these simple elements which creates the apparatus and methods, within the ambit of the present invention. Descriptions of preferred embodiments of the invention follow. However, it is to be understood that the best mode descriptions do not limit the scope of the present invention.

DESCRIPTION OF THE PREFERRED EMBODIMENTS

Although the disclosure hereof is detailed to enable those skilled in the art to practice the invention, the embodiments published herein merely exemplify the present invention.

In the most general sense, the present invention is an implant for bone where the implant is adapted for connection with a device distinct from the implant. Among other things, the current invention can be adapted for use with vertebra or other bone tissues. The present implant is particularly adapted for use in the cervical region of the spine. The current invention can be provided with a conduit for transporting biocompatible devices/substances or chemotherapeutic agents, such as adhesives, cameras, cannulas, fiber optics, implants, pharmaceuticals, etc. Dispersion of adhesives from the windows or openings of the implant before closing the surgical wound, reduces the risk of the fastener backing out of the wound prior to the fastener fully interlocking with tissue overgrowth. Polymethymethacrylate is an adhesive particularly well suited for use with the current fastener.

Preferred embodiments of the present invention are manufactured of titanium alloys, stainless steel, non-resorbable polymers or any other composition acceptable in the art. Within the scope of the present invention, it has advantageously been discovered that cylindrical shafts (40) can have lengths from about 2 to about 10 millimeters; polyaxial heads (50) can have lengths of from about 5 millimeters to about 25 millimeters; sockets (54) of polyaxial heads (50) can have depths from about 3 millimeters to about 23 millimeters, diameters from about 4 millimeters to about 20 millimeters, lateral openings widths (62, 64) from about 3 millimeters to about 10 millimeters; and blades (80, 120) can have lengths of from about 3 millimeters to about 12 millimeters, widths of from about 4 millimeters to about 10 millimeters and heights of from about 0.2 millimeters to about 4 millimeters.

Figure 1:
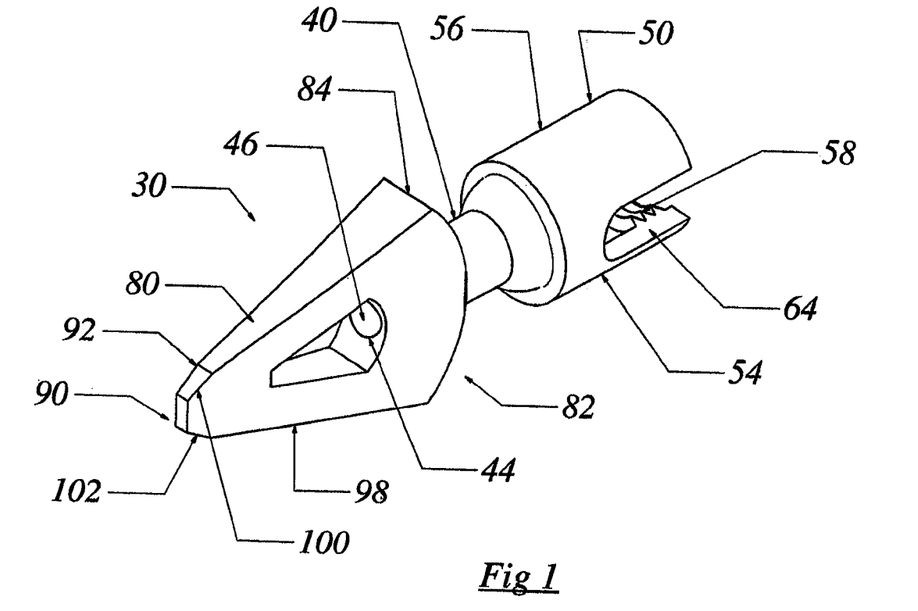
FIG. 1 is a perspective of a first preferred embodiment of the implant.
Figure 2:
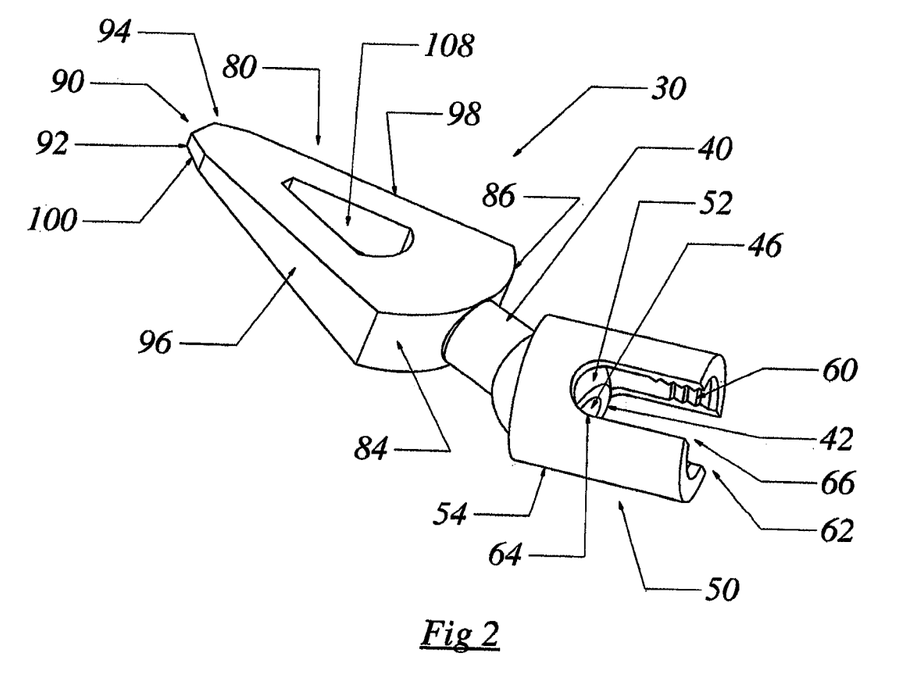
FIG. 2 is a perspective of a first preferred embodiment of the implant.

FIGS. 1 and 2 are perspectives of a first preferred embodiment of implant (30). Within the scope of the current invention, implant (30) can be interconnected with a device distinct from the implant. It has been discovered that implant (30) is useful for spinal surgeries, and, in particular, surgeries for the cervical region of the spine.

Among other things, the preferred embodiment of implant (30), enabled in FIGS. 1 and 2, includes cylindrical shaft (40), polyaxial head (50) and blade (80). Cylindrical shaft (40) includes first end (42), second end (44) and inner cavity (46) extending through first end (42) and second end (44).

Polyaxial head (50) of implant (30) is adapted for connection with a device (not shown) distinct from implant (30). Examples of devices connectable to polyaxial head (40) include but are not limited to: rods, bars, cross-links, screws and locking nuts. Polyaxial head (50) is provided with spheroid (52) connected to first end (42) of cylindrical shaft (40) and socket (54) connected to spheroid (52). Prior to surgical fixation, the combination of spheroid (52) and socket (54) allows polyaxial head (50) to be moved in a multitude of axes relative to the inner cavity (46) of cylindrical shaft (40). Socket (54) is provided with an outward housing (56) and inward receptacle (58) including one or more threads (60). Selected preferred embodiments of housing (56) can be provided with openings (62, 64, 66) adapted to receive one or more devices distinct from implant (30).

Arcuate side (82) of blade (80) is connected with second side (44) of cylindrical shaft (40). Arcuate side (82) of blade (80) is of a dimension wider than the diameter of cylindrical shaft (40). Arcuate side (82) includes first wing (84) and second wing (86) where each wing (84, 86) extends away from the longitudinal axis of cylindrical shaft (40). As shown in FIGS. 1 and 2, each wing (84, 86) is arched away from first end (42) of cylindrical shaft (40).

Straight side (90) of blade (80) is of lesser length than arcuate side (82) and positioned opposite from arcuate side (82). Straight side (90) includes first end (92) and second end (94). First converging edge (96) connected to first wing (84) and second converging edge (98) connected second wing (86) converge toward each other as the converging edges (96, 98) approach straight side (90). Select preferred embodiments of the current invention can be provided with first transitional edge (100) connected to first end (92) of straight side (90) and first converging edge (96) and second transitional edge (102) second end (94) of straight side (90) and converging edge (98). Within the scope of the current invention, select preferred embodiments of implant (30) are not provided with transitional edges (100, 102) and converging edges (96, 98) are connected directly to first end (92, 94) of straight side (90). Regarding the current implant (30), straight side (90), converging edges (96, 98) and transitional edges (100, 102) are adapted to surgically cut bone and other tissues.

Implant (30) is provided with aperture (108) proximate the center of blade (80). Post implantation, the combination of aperture (108) and inner cavity (46) of cylindrical shaft (40), among other things, allows the surgeon to remove unwanted debris from the surgical wound or introduce adhesive, antimicrobial, osteogenic or chemotherapeutic substances into the surgically created cavity.

Figure 3:
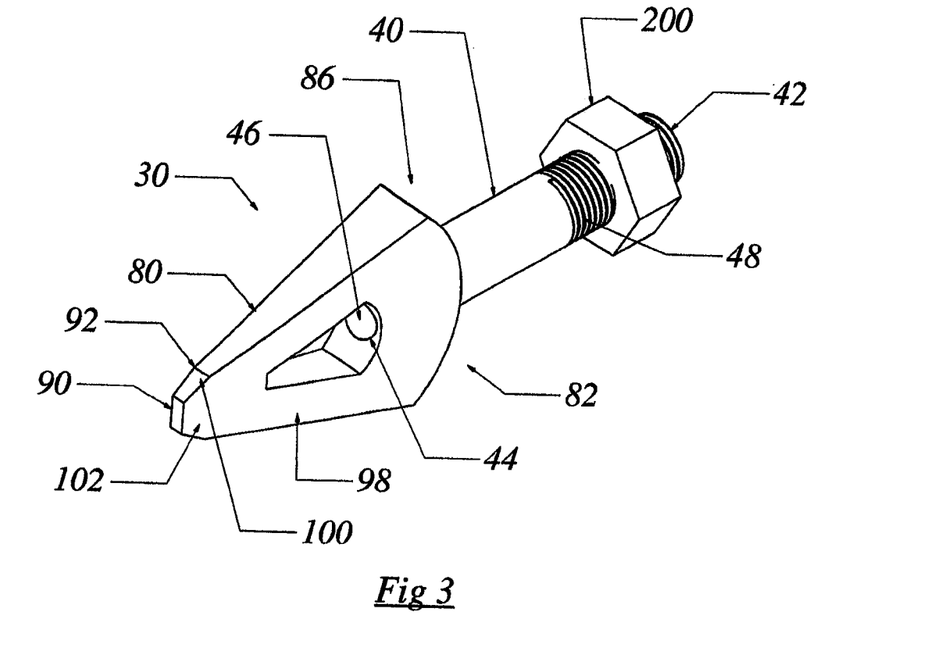
FIG. 3 is a perspective of a second preferred embodiment of the implant.
Figure 4:
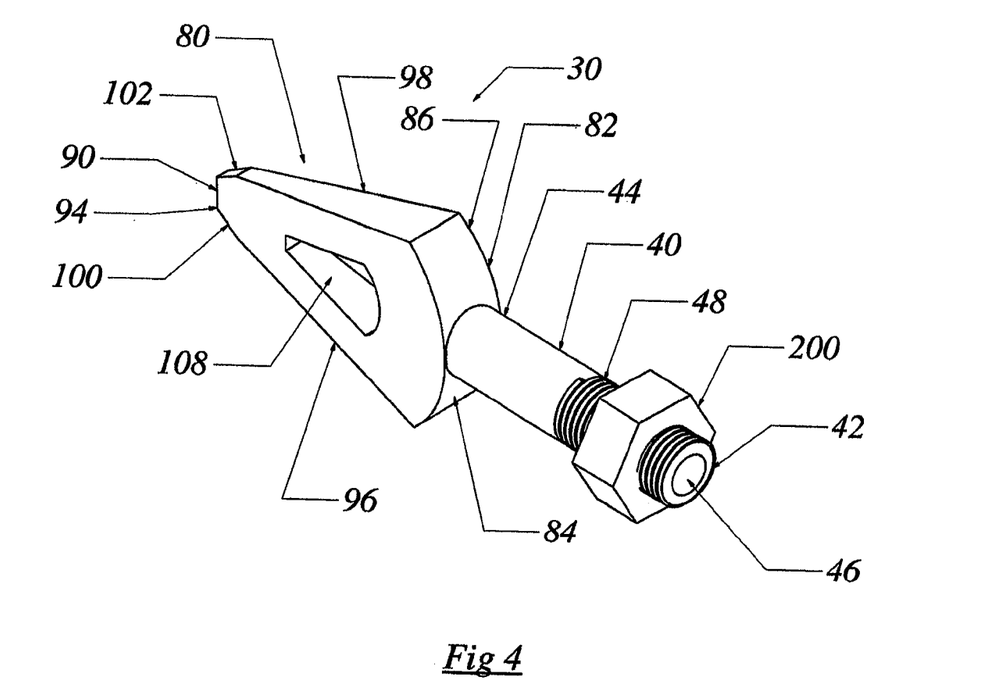
FIG. 4 is a perspective of a second preferred embodiment of the implant.

FIGS. 3 and 4 are perspectives of a second preferred embodiment of implant (30). Within the scope of the current invention, implant (30) can be interconnected with a device distinct from the implant, such as a nut (200) or other device (not shown) for coupling with implant (30). It has been discovered that implant (30) is useful for spinal surgeries, and, in particular, surgeries for the cervical region of the spine.

Among other things, the preferred embodiment of implant (30), enabled in FIGS. 3 and 4, includes cylindrical shaft (40) and blade (80). Cylindrical shaft (40) includes first end (42), second end (44) and inner cavity (46) extending through first end (42) and second end (44). First end (42) of cylindrical shaft (40) is provided with thread (48) that can be utilized to connect implant (30) to a device distinct from implant (30). Thread (48) runs about at least a portion of the outward side of cylindrical shaft (40) and advances from first end (42) toward the second end (44) of cylindrical shaft (40).

Arcuate side (82) of blade (80) is connected with second side (44) of cylindrical shaft (40). Arcuate side (82) of blade (80) is of a dimension wider than the diameter of cylindrical shaft (40). Arcuate side (82) is also provided with first wing (84) and second wing (86) where each wing (84, 86) extends away from the longitudinal axis of cylindrical shaft (40). As shown in FIGS. 1 and 2, each wing (84, 86) is arched away from first end (42) of cylindrical shaft (40).

Straight side (90) of blade (80) is of lesser length than arcuate side (82) and positioned opposite from arcuate side (82). Straight side (90) includes first end (92) and second end (94). First converging edge (96) connected to first wing (84) and second converging edge (98) connected second wing (86) converge toward each other as the converging edges (96, 98) approach straight side (90). Select preferred embodiments of the current invention can be provided with first transitional edge (100) connected to first end (92) of straight side (90) and first converging edge (96) and second transitional edge (102) second end (94) of straight side (90) and converging edge (98). Within the scope of the current invention, select preferred embodiments of implant (30) are not provided with transitional edges (100, 102) and converging edges (96, 98) are connected directly to first end (92, 94) of straight side (90). Regarding the current implant (30), straight side (90), converging edges (96, 98) and transitional edges (100, 102) are adapted to surgically cut bone and other tissues.

Implant (30) is provided with aperture (108) proximate the center of blade (80). Post implantation, the combination of aperture (108) and inner cavity (46) of cylindrical shaft (40), among other things, allows the surgeon to remove unwanted debris from the surgical wound or introduce adhesive, antimicrobial or osteogenic substances into the surgically created cavity.

Figure 5:
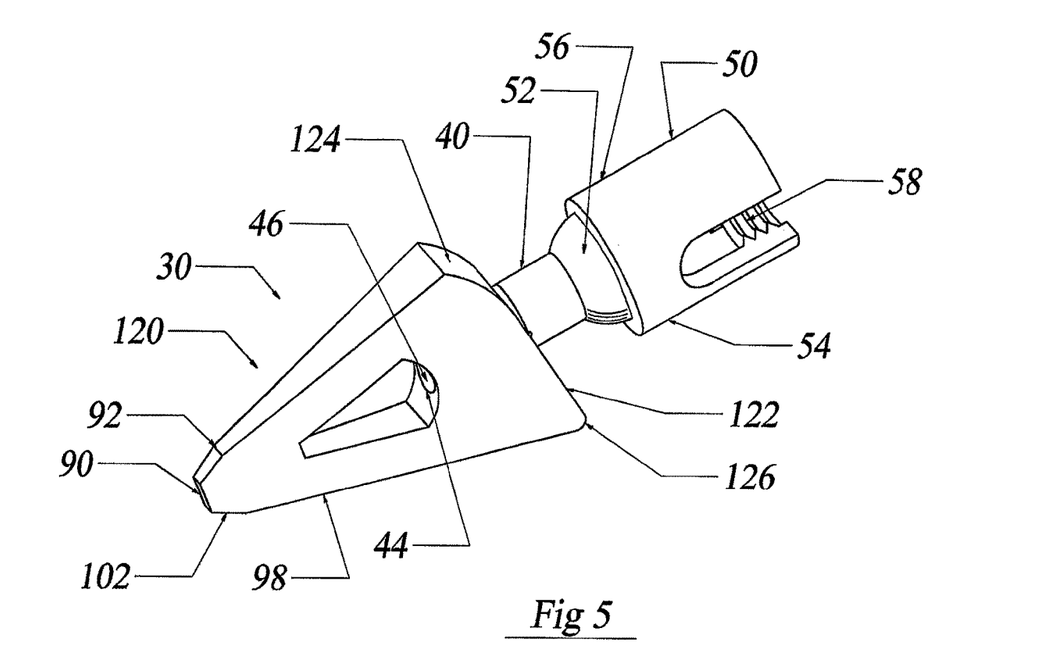
FIG. 5 is a perspective of a third preferred embodiment of the implant.
Figure 6:
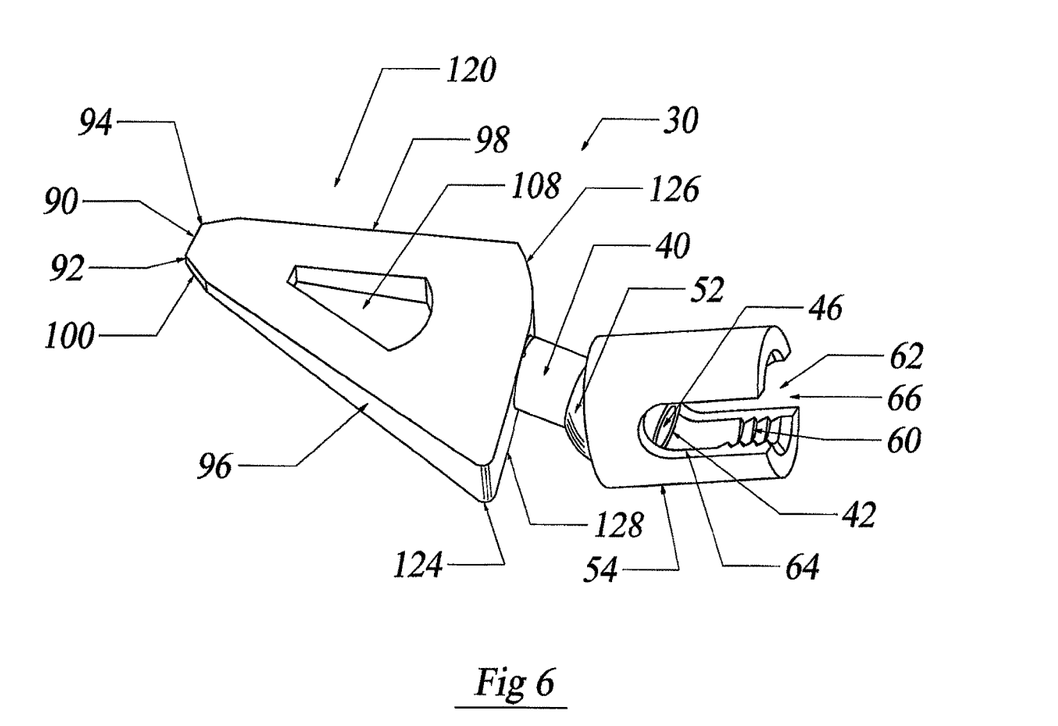
FIG. 6 is a perspective of a third preferred embodiment of the implant.

FIGS. 5 and 6 are perspectives of a third preferred embodiment of implant (30). Within the scope of the current invention, implant (30) can be interconnected with a device distinct from the implant. It has been discovered that implant (30) is useful for spinal surgeries, and, in particular, surgeries for the cervical region of the spine.

Among other things, the preferred embodiment of implant (30), enabled in FIGS. 5 and 6, includes cylindrical shaft (40), polyaxial head (50) and blade (120). Cylindrical shaft (40) includes first end (42), second end (44) and inner cavity (46) extending through first end (42) and second end (44).

Polyaxial head (50) of implant (30) is adapted for connection with a device (not shown) distinct from implant (30). Examples of devices connectable to polyaxial head (50) include but are not limited to: rods, cross-links, bars, screws, and locking nuts. Polyaxial head (50) is provided with spheroid (52) connected to first end (42) of cylindrical shaft (40) and socket (54) connected to spheroid (52). Prior to surgical fixation, the combination of spheroid (52) and socket (54) allows polyaxial head (50) to be moved in a multitude of axes relative to the longitudinal axis or inner cavity (46) of cylindrical shaft (40). Socket (54) is provided with an outward housing (56) and inward receptacle (58) including one or more threads (60). Selected preferred embodiments of housing (56) can be provided with openings (62, 64, 66) adapted to receive one or more devices distinct from implant (30).

Slanted side (122) of blade (120) is connected with second side (44) of cylindrical shaft (40). Slanted side (122) of blade (120) is of a dimension wider than the diameter of cylindrical shaft (40). Slanted side (122) includes first wing (124) and second wing (126) where each wing (124, 126) extends away from the longitudinal axis of cylindrical shaft (40). As shown in FIGS. 5 and 6, a first one of the wings (124, 126) is arcuate and arched away from the first end cylindrical shaft (40). A second one of the wings (124, 126) is provided with a pitched plane (128) facing first end (42) of cylindrical shaft (40). The combination of an arcuate wing and a wing including a pitched plane creates an asymmetric blade (120). Pitched plane (128) intersects the longitudinal axis of implant (30) at an angle of between five and eighty five degrees as measured from the distal point of pitched plane (128) to the intersection of pitched plane and implant's (30) longitudinal axis.

Straight side (90) of blade (120) is of lesser length than slanted side (122) and positioned opposite from slanted side (122). Straight side (90) includes first end (92) and second end (94). First converging edge (96) connected to first wing (124) and second converging edge (98) connected second wing (126) converge toward each other as the converging edges (96, 98) approach straight side (90). Select preferred embodiments of the current invention can be provided with first transitional edge (100) connected to first end (92) of straight side (90) and first converging edge (96) and second transitional edge (102) second end (94) of straight side (90) and converging edge (98). Within the scope of the current invention, select preferred embodiments of implant (30) are not provided with transitional edges (100, 102) and converging edges (96, 98) are connected directly to first end (92, 94) of straight side (90). Regarding the current implant (30), straight side (90), converging edges (96, 98) and transitional edges (100, 102) are adapted to surgically cut bone and other tissues.

Implant (30) is provided with aperture (108) proximate the center of blade (80). Post implantation, the combination of aperture (108) and inner cavity (46) of cylindrical shaft (40), among other things, allows the surgeon to remove unwanted debris from the surgical wound or introduce adhesive, antimicrobial or osteogenic substances into the surgically created cavity.

Figure 7:
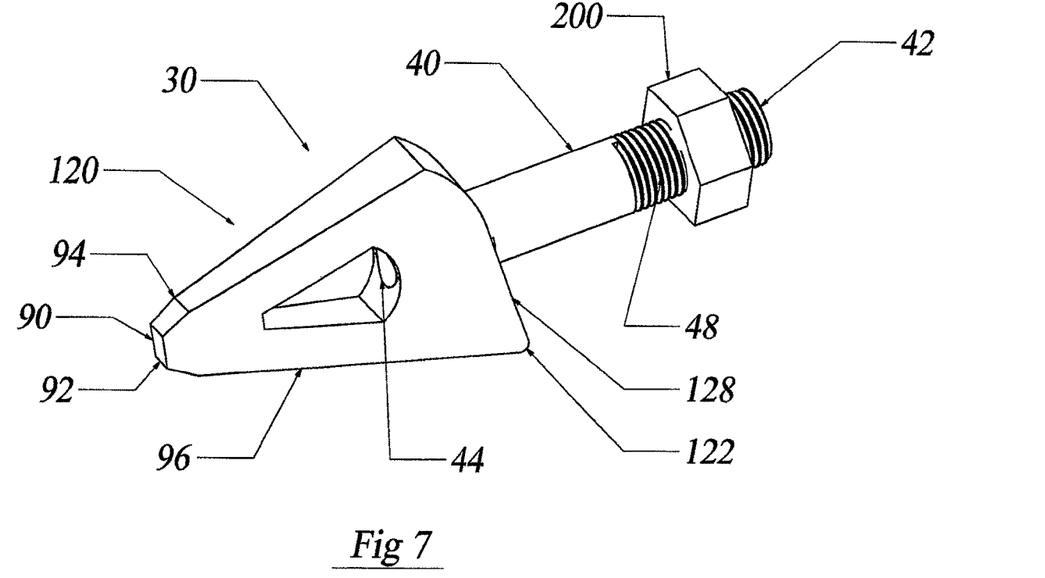
FIG. 7 is a perspective of a fourth preferred embodiment of the implant.
Figure 8:
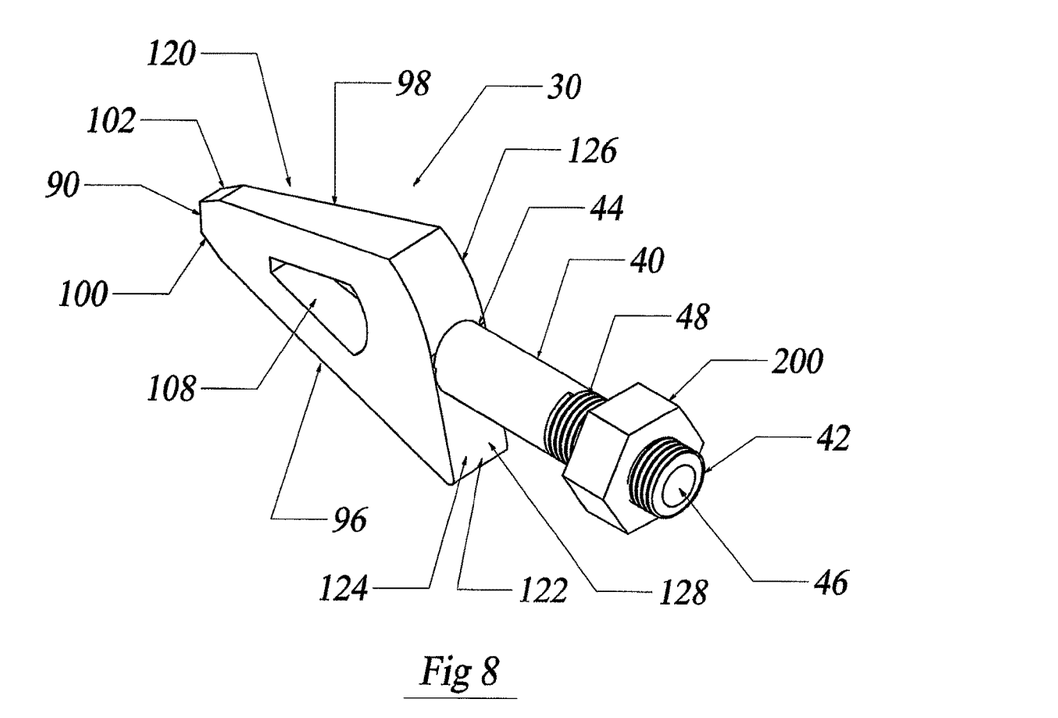
FIG. 8 is a perspective of a fourth preferred embodiment of the implant.
Figure 9:
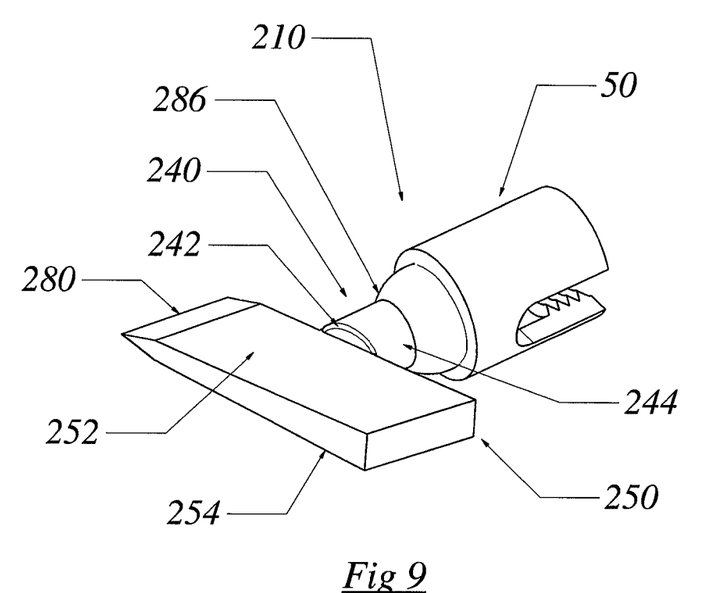
FIG. 9 is a perspective of a fifth preferred embodiment of the implant.
Figure 10:
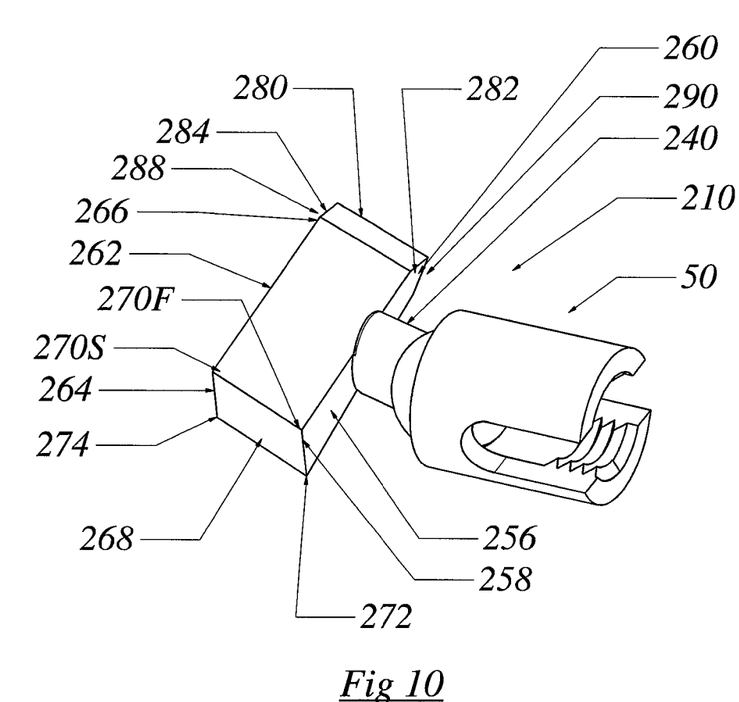
FIG. 10 is a perspective of a fifth preferred embodiment of the implant.
Figure 11:
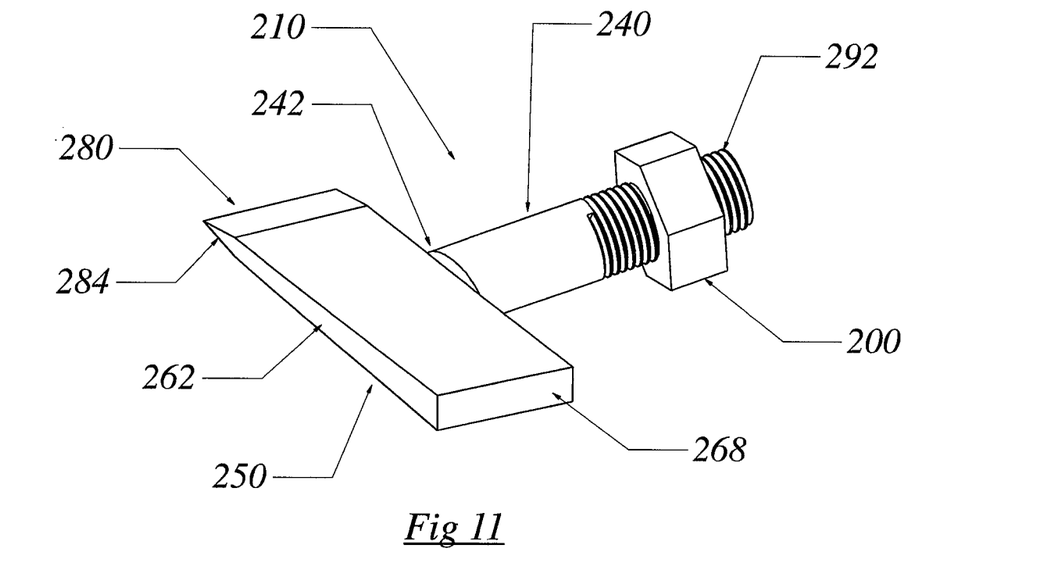
FIG. 11 is a perspective of a fifth preferred embodiment of the implant.
Figure 12:
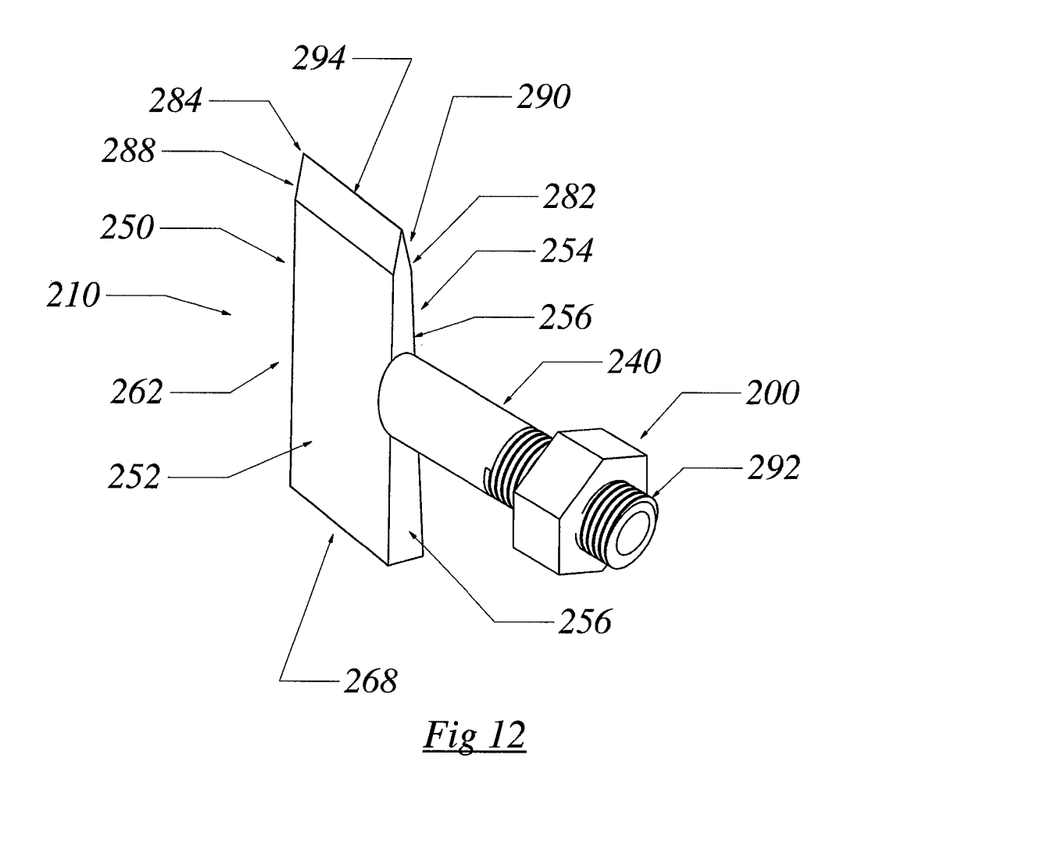
FIG. 12 is a perspective of a fifth preferred embodiment of the implant.
Figure 13:
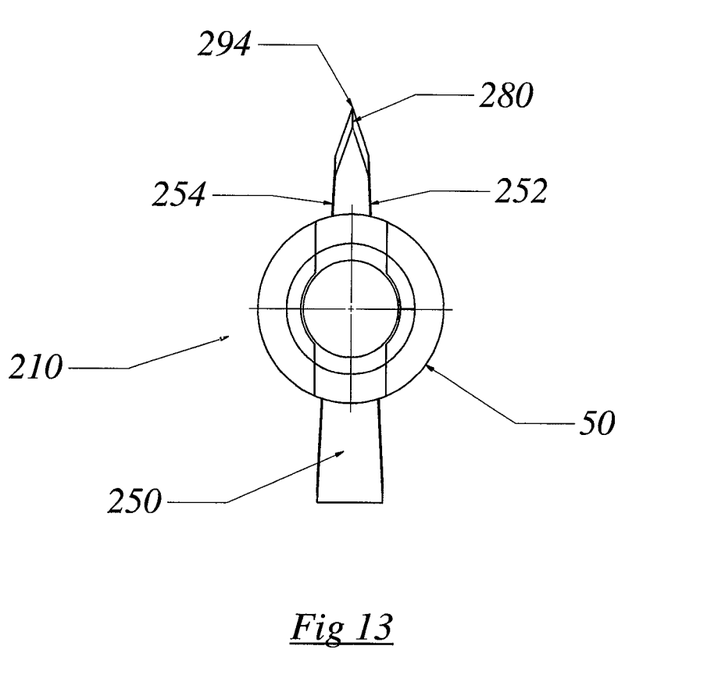
FIG. 13 is a frontal view with polyaxial head closer to the viewer.
Figure 14:
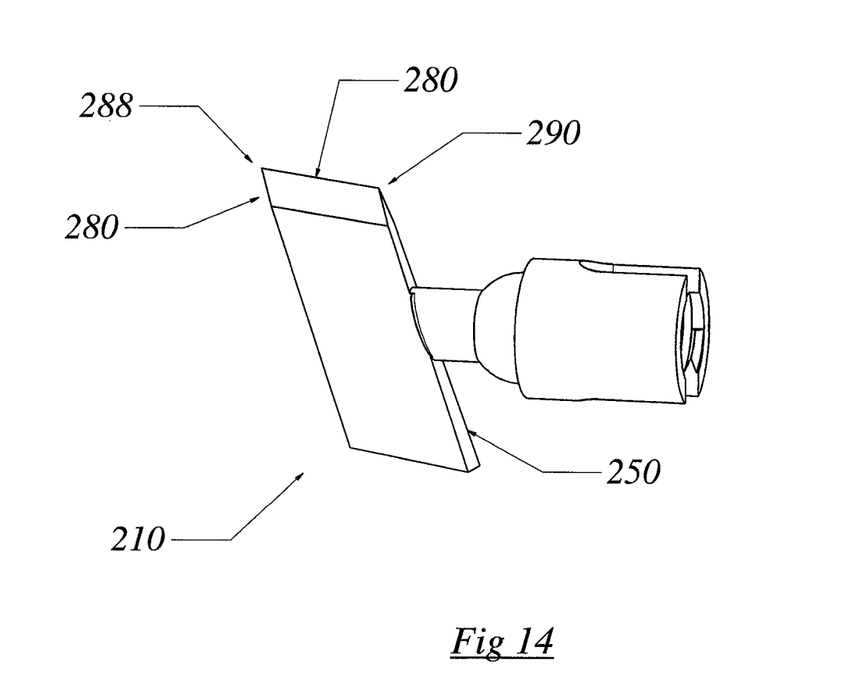
FIG. 14 is a perspective of a fifth preferred embodiment of the implant.
Figure 15:
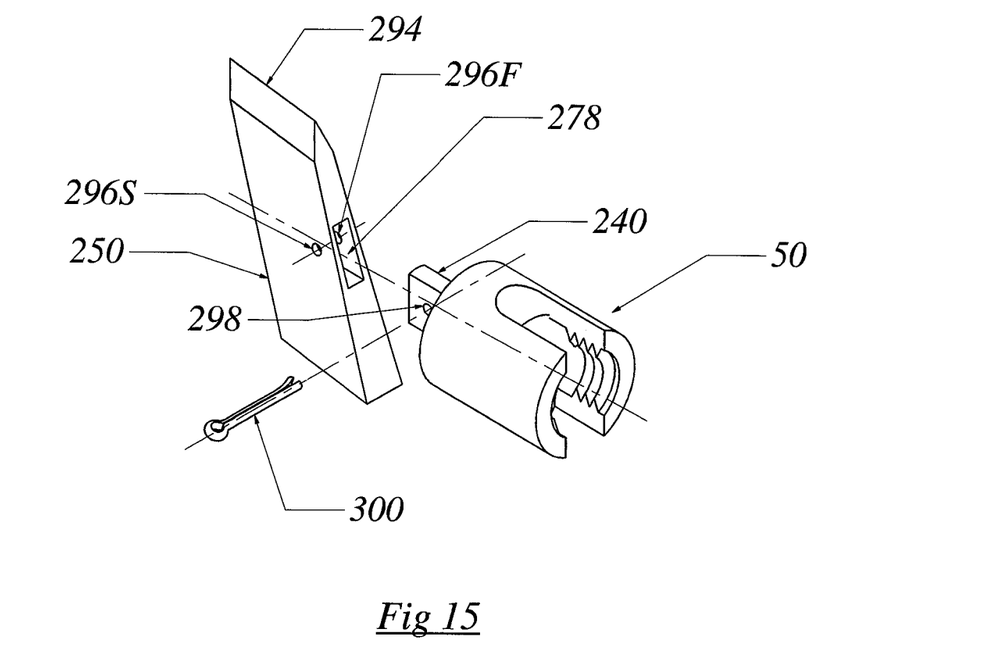
FIG. 15 is a perspective of a sixth preferred embodiment of the implant.
Figure 16:
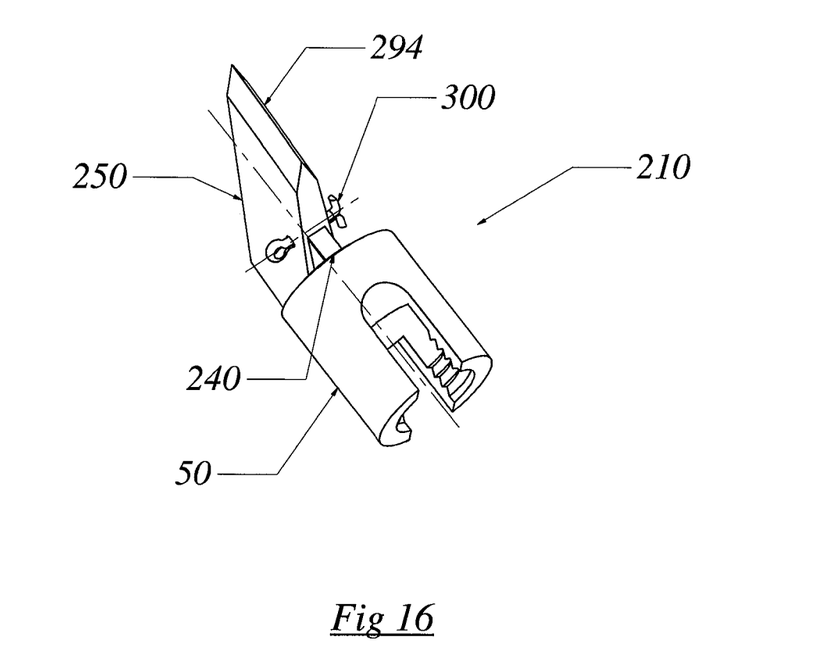
FIG. 16 is a perspective of a sixth preferred embodiment of the implant.
Figure 17:
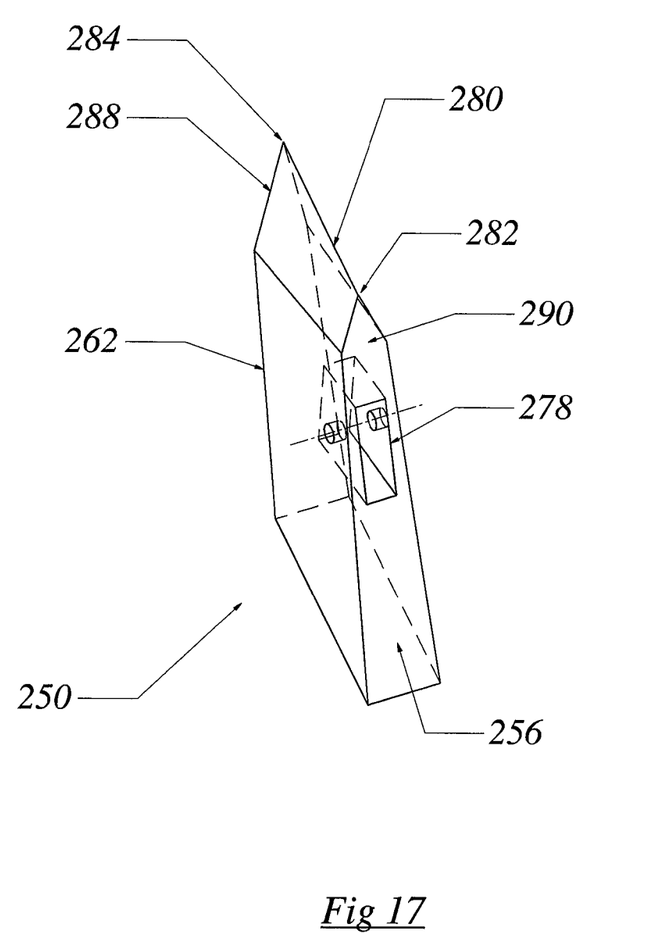
FIG. 17 is another perspective of the surgical cutting wedge.

FIGS. 7 and 8 are perspectives of a fourth preferred embodiment of implant (30). Within the scope of the current invention, implant (30) can be interconnected with a device distinct from the implant, such as a nut (200) or other device (not shown) for coupling with implant (30). It has been discovered that implant (30) is useful for spinal surgeries, and, in particular, surgeries for the cervical region of the spine.

Among other things, the preferred embodiment of implant (30), enabled in FIGS. 7 and 8, includes cylindrical shaft (40) and blade (120). Cylindrical shaft (40) includes first end (42), second end (44) and inner cavity (46) extending through first end (42) and second end (44). First end (42) of cylindrical shaft (40) is provided with thread (48) that can be utilized to connect implant (30) to a device distinct from implant (30). Thread (48) runs about at least a portion of the outward side of cylindrical shaft (40) and advances from first end (42) toward the second end (44) of cylindrical shaft (40).

Slanted side (122) of blade (120) is connected with second side (44) of cylindrical shaft (40). Slanted side (122) of blade (120) is of a dimension wider than the diameter of cylindrical shaft (40). Slanted side (122) includes first wing (124) and second wing (126) where each wing (124, 126) extends away from the longitudinal axis of cylindrical shaft (40). As shown in FIGS. 7 and 8, a first one of the wings (124, 126) is arcuate and arched away from the first end cylindrical shaft (40). A second one of the wings (124, 126) is provided with a pitched plane (128) facing first end (42) of cylindrical shaft (40). The combination of an arcuate wing and a wing including a pitched plane creates an asymmetric blade (120). Pitched plane (128) intersects the longitudinal axis of implant (30) at an angle of between five and eighty five degrees as measured from the distal point of pitched plane (128) to the intersection of pitched plane and implant's (30) longitudinal axis.

Straight side (90) of blade (120) is of lesser length than slanted side (122) and positioned opposite from slanted side (122). Straight side (90) includes first end (92) and second end (94). First converging edge (96) connected to first wing (124) and second converging edge (98) connected second wing (126) converge toward each other as the converging edges (96, 98) approach straight side (90). Select preferred embodiments of the current invention can be provided with first transitional edge (100) connected to first end (92) of straight side (90) and first converging edge (96) and second transitional edge (102) second end (94) of straight side (90) and converging edge (98). Within the scope of the current invention, select preferred embodiments of implant (30) are not provided with transitional edges (100, 102) and converging edges (96, 98) are connected directly to first end (92, 94) of straight side (90). Regarding the current implant (30), straight side (90), converging edges (96, 98) and transitional edges (100, 102) are adapted to surgically cut bone and other tissues.

Implant (30) is provided with aperture (108) proximate the center of blade (80). Post implantation, the combination of aperture (108) and inner cavity (46) of cylindrical shaft (40), among other things, allows the surgeon to remove unwanted debris from the surgical wound or introduce adhesive, antimicrobial or osteogenic substances into the surgically created cavity.

Within the scope of the current present invention, select preferred embodiments can be provided with a surgical wedge cutter (250) and a permanent shaft (240) or a releasable shaft (240).

FIGS. 9-17 portray a fifth and sixth embodiments of the current invention. Implant (210) is adapted for interconnection with a device distinct from the implant (210). Examples of devices connectable to implant (210) include but are not limited to: rods, bars, cross-links, screws and locking nuts.

Implant (210) includes shaft (240) and surgical cutting wedge (250). In accordance with the present invention, cutting edge (280) of cutting wedge can cut in perpendicular, clockwise and counterclockwise directions relative shaft (240). By way of illustration, longitudinal motion of cutting edge (280) can penetrate and slice tissue(s) perpendicular to shaft (240) while rotation of shaft causes cutting edge (280) to cut tissue(s) in either a clockwise or counterclockwise directions.

Shaft (240) has a first end (242) and a second end (244) opposite the first end (242). Select preferred embodiments of implant (210) can include a second end (286) of shaft (240) comprises a thread (292). Other preferred embodiments of implant (210) can include a polyaxial head (50) connected to second end (286) of shaft (240). Still other preferred embodiments of implant (210) include detachable shaft (240) comprising a first end (242) releasably connected to catch (278) of surgical cutting wedge (250).

Surgical cutting wedge (250) is connected to the first end (242) of the shaft (240). Within the ambit of the current invention, surgical cutting wedge (250) can be provided with first planar surface (252) and second planar surface (254). In select preferred embodiments, first side (256) of surgical cutting wedge (250) is connected with and perpendicular to the shaft (240). First side (256) of surgical wedge (250) has a first end (258) of greater height than an opposed second end (260) of first side (256). Second side (262) of surgical wedge (250) is parallel to the first side (256) and first end (264) of second side (262) is of greater height than opposed second end (266) of second side (262). Third side (268) of surgical cutting wedge (250) extends between the first and second planar surfaces (252, 254) and first and second sides (256, 262). In select preferred embodiments of implant (210), first and second planar surfaces (252, 254) can be parallelograms. Connection angles (270F, 270S) of first and second sides (256, 262) with opposed ends (272, 274) of the third side (268) can be identical.

First end (242) of detachable shaft (240) can include opening (298) extending through detachable shaft (240). Surgical cutting wedge (250) can be provided with opposed orifices (296F, 296S) extending from the catch (278) through the first and second planar surfaces (252, 254). Placement of pin (300) through opposed orifices (296F, 296S) and opening (298) secures detachable shaft (240) to catch (278) of surgical cutting wedge (250). In accordance with the current invention, pin (300) can be a cotter-type pin with bendable tips.

Cutting edge (280) of surgical cutting wedge (250) can be opposed from and parallel to the third side (268) and connected to the first planar surface (252), the second planar surface (254) and the second ends (282, 284) of the first and second sides (256, 262). Slopes of first planar surface (252) and second planar surface (254) from the third side (268) to the cutting edge (280) can be utilized to establish one or more angles of surgical cutting wedge (250). Preferred embodiments of cutting edge (280) can include bevel (294).

Select preferred embodiments of cutting edge (280) have elevations of cutting edge (280) that are graduated from a greater height to a lesser height as the cutting edge (280) traverses from an outward margin (288) of the second end (284) of the second side (262) toward outward margin (290) of the second end (282) of the first side (256).

Applicant has enabled, described and disclosed the invention as required by the Patent Cooperation Treaty and Title 35 of the United States Code.

What is claimed is:
1. An implant for bone adapted for interconnection with a device distinct from the implant; the implant comprising:
   a) a shaft comprising a first end and a second end opposite the first end; and
   b) a surgical cutting wedge connected to the first end of the shaft; the surgical cutting wedge comprising:
      i) a first planar surface and a second planar surface;
      ii) a first side connected with and perpendicular to the shaft, wherein the first side comprises a first end of greater height than an opposed second end of first side;
      iii) a second side parallel to the first side, wherein a first end is of greater height than an opposed second end of second side;
      iv) a planar third side extending between the first and second planar surfaces and first and second sides, wherein connection angles of first and second sides with opposed ends of the planar third side are identical; and
      v) a cutting edge opposed from and parallel to the planar third side; the cutting edge connected to the first planar surface, the second planar surface and the second ends of the first and second sides.

2. The implant of claim 1, wherein the cutting edge comprises a bevel.

3. The implant of claim 2, wherein the first and second planar surfaces are parallelograms.

4. The implant of claim 3, wherein elevations of the cutting edge are graduated from a greater height to a lesser height as the cutting edge traverses from an outward margin of the second end of the second side toward outward margin of the second end of the first side.

5. The implant of claim 3 further comprising a polyaxial head connected to the second end of the shaft.

6. The implant of claim 3, wherein the second end of shaft comprises a thread.

7. An implant for bone adapted for interconnection with a device distinct from the implant; the implant comprising:
   a) a surgical cutting wedge comprising:
      i) a first planar surface and a second planar surface;
      ii) an interconnected combination of a first side, a second side and a third side; the interconnected combination of the first, second and third sides extending between and connected to the first and second planar surfaces, wherein: the first side comprises a first end of greater height than an opposed second end of first side; and the second side comprises a first end of greater height than an opposed second end of second side; and
      iii) a cutting edge connected to the first and second planar surfaces and the second ends of the first and second sides such that the cutting edge is adapted to cut in perpendicular, clockwise and counterclockwise directions relative to a shaft; and
   b) a first end of the shaft connected to the first side at a position between the opposed cutting edge and third side of the surgical cutting wedge.

8. The implant of claim 7, wherein the cutting edge comprises a bevel.

9. The implant of claim 8, wherein the first and second planar surfaces are parallelograms.

10. The implant of claim 9, wherein elevations of the cutting edge are graduated from a greater height to a lesser height as the cutting edge traverses from an outward margin of the second end of the second side toward outward margin of the second end of the first side.

11. The implant of claim 9 further comprising a polyaxial head connected to the second end of the shaft.

12. The implant of claim 9, wherein the second end of shaft comprises a thread.

\* \* \* \* \*